United States Patent [19]
Gorycki et al.

[11] Patent Number: 5,939,447
[45] Date of Patent: Aug. 17, 1999

[54] SUBSTITUTED BENZOPYRANS

[75] Inventors: Peter D. Gorycki, Conshohocken; Blanche W. Annan, West Chester, both of Pa.; George Y. Kuo, Cherry Hill, N.J.

[73] Assignee: SmithKline Beecham Corporation, Philadelphia, Pa.

[21] Appl. No.: 08/894,956

[22] PCT Filed: Dec. 20, 1996

[86] PCT No.: PCT/US96/20607

§ 371 Date: Mar. 11, 1998

§ 102(e) Date: Mar. 11, 1998

[87] PCT Pub. No.: WO97/25040

PCT Pub. Date: Jul. 17, 1997

[51] Int. Cl.$^6$ .......................... A61K 31/41; C07D 405/04
[52] U.S. Cl. .............................. 514/382; 548/253
[58] Field of Search .............................. 548/253; 514/382

[56] References Cited

U.S. PATENT DOCUMENTS 5,596,103   1/1997   Johnson et al. ..................... 548/253

*Primary Examiner*—Robert W. Ramsuer
*Attorney, Agent, or Firm*—James M. Kanagy; Charles M. Kinzig

[57] ABSTRACT

This invention covers certain hydroxy-substituted benzopyrans which are useful for treating asthma and other diseases involving leukotriene-related disease states.

6 Claims, No Drawings

SUBSTITUTED BENZOPYRANS

This application is a 371 of PCT/U.S. Ser. No. 96/20607 filed Dec. 20, 1996.

SCOPE OF THE INVENTION

This invention covers certain benzopyran compounds which have activity as leukotriene antagonists and are active metabolites of an anti-asthma drug named pranlukast.

AREA OF THE INVENTION

Substituted benzopyran compound which have activity as leukotriene antagonists are known in the art. For example U.S. Pat. No. 4,780,469 which corresponds to Japanese patent 1741466 and EP patent EP O 173 516-A discloses a class of benzopyrans which are described as antagonists of the leukotrienes, particularly the peptido-leukotrienes $LTC_4$, $LTD_4$, and $LTE_4$. As such, these compounds are useful for treating a host of diseases associated with modification of the metabolic pathway which has these leukotrienes as intermediates. An example of such diseases is asthma.

This invention relates to an benzylhydroxybenzopyran and arylhydroxybenzopyran as illustrated by Formula I and II respectively.

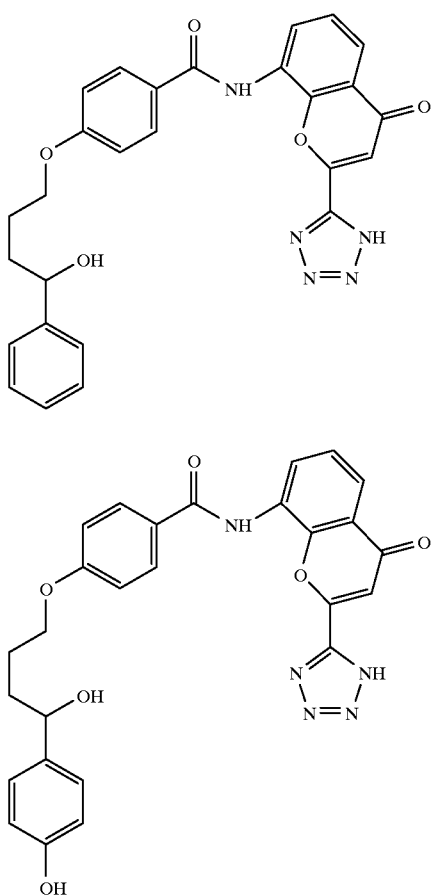

Formula I is named 4-oxo-8-[4-(4-hydroxy-4-phenylbutoxy)benzoylamino]-2-tetrazol-5-yl-4H-1-benzopyran.

Formula II is named 4-oxo-8-[4-(4-hydroxy-4-(4-hydroxyphenyl)butoxy)benzoylarnino]-2-tetrazol-5-yl-4H-1-benzopyran.

This invention also relates to an essentially pure preparation of a compound of formula I or II, or a pharmaceutical composition of one and/or the other in combination with a pharmaceutically acceptable excipient. It also relates to a method for manufacturing a medicarnent for treating a disease such as asthma using fornula I or II, or an essentially pure form thereof. These compounds are useful in treating asthma. Hydrates, solvates, tautomeric forms, isomers and polymorphs of these compounds are also included with the scope of this invention.

DETAILED DESCRIPTION OF THE INVENTION

These two compounds may be prepared by synthetic chemistry means or can be obtained by extracting them from biological samples collected from mammals which have been given the compound 8-[p-(4-phenylbutyloxy)benzoyl] amino-2-tetrazol-5'-yl)-4-oxo-4H-1-benzopyran (pranlukast). A synthetic process for one of the compounds is given below; the other can be isolated from biological sources as further described below. The compound named in the preceeding sentence can be made by the chemistries set out in U.S. Pat. No. 4,780,469 which corresponds to Japanese patent 1741466 and EP patent EP O 173 516-A.

The benzylic hydroxylation (Formula (I)) of pranlukast appears to be a major route of metabolism in humans. This metabolism results in measurable plasma concentrations in humans. Results from a human radiolabel study suggests that 98.4% of the administered radiolabel is recovered in feces (~84% as pranlukast, 6.6% as an arylhydroxy metabolite [Formula (II)] and about 6% as benzylhydroxy metabolite [Formula (I)]. The arylhydroxy and benzylhydroxy metabolic pathways appear to be the two major metabolitic routes of pranlukast metabolism in humans and when considering the poor absorption of pranlukast, the quantities of these metabolites measured in feces may represent the total of absorbed and metabolized parent.

In incubations of liver microsomes from rats or mice, the arylhydroxy and benzylhydroxy metabolites are detectable when using high concentrations of pranlukast (50 uM), but hydrolysis of the amide bond in the center of the molecule is the predominant metabolic pathway in these rodent incubations. Liver microsomes from dogs form the arylhydroxy species and only very small amounts of the benzyl species.

The arylhydroxy and benzylhydroxy metabolites are measurable in human plasma, but only limited data are available from the single radiolabelled study. The arylhydroxy metabolite appears to be sulfated in humans but there is no evidence for sulfation of the benzylhydroxy metabolite. From an evaluation of a battery of human liver microsomes, it was evident that some human livers have enhanced activity towards benzylic hydroxylation. It appears that benzylic and aryl hydroxylation are performed by different P450 enzymes but which enzyme(s) is currently not known.

As regards the pharmacological activity of Formula I and II both have been found to be active in assays predictive of utility in treating asthma and other diseases which can be treated by pranlukast.

It will be recognized that both compounds may exist in both racemic and optically active forms. Both forms are to be considered to be within the scope of the present invention.

Pharmaceutically acceptable salts are prepared in a standard manner. The hydrogen on the tetrazole ring is sufficiently acidic so as to form salts at a pH of about 6–7 or higher.

Pharmaceutical compositions of the present invention comprise a pharmaceutical carrier or diluent and some amount of a compound of the formula (I) or (II). The compound may be present in an amount to effect a physiological response, or it may be present in a lesser amount such that the user will need to take two or more units of the composition to effect the treatment intended. These compositions may be made up as a solid, liquid or in a gaseous form. Or one of these three forms may be transformed to another at the time of being administered such as when a solid is delivered by aerosol means, or when a liquid is delivered as a spray or aerosol.

The nature of the composition and the pharmaceutical carrier or diluent will, of course, depend upon the intended route of administration, for example parenterally, topically, orally or by inhalation.

For topical administration the pharmaceutical composition will be in the form of a cream, ointment, liniment, lotion, pastes, aerosols, and drops suitable for administration to the skin, eye, ear, or nose.

For parenteral administration the pharmaceutical composition will be in the form of a sterile injectable liquid such as an ampule or an aqueous or non-aqueous liquid suspension.

For oral administration the pharmaceutical composition will be in the form of a tablet, capsule, powder, pellet, atroche, lozenge, syrup, liquid, or emulsion.

When the pharmaceutical composition is employed in the form of a solution or suspension, examples of appropriate pharmaceutical carriers or diluents include: for aqueous systems, water; for non-aqueous systems, ethanol, glycerin, propylene glycol, corn oil, cottonseed oil, peanut oil, sesame oil, liquid parafins and mixtures thereof with water; for solid systems, lactose, kaolin and mannitol; and for aerosol systems, dichlorodifluoromethane, chlorotrifluoroethane and compressed carbon dioxide. Also, in addition to the pharmaceutical carrier or diluent, the instant compositions may include other ingredients such as stabilizers, antioxidants, preservatives, lubricants, suspending agents, viscosity modifiers and the like, provided that the additional ingredients do not have a detrimental effect on the therapeutic action of the instant compositions.

The pharmaceutical preparations thus described are made following the conventional techniques of the pharmaceutical chemist as appropriate to the desired end product.

In these compositions, the amount of carrier or diluent will vary but preferably will be the major proportion of a suspension or solution of the active ingredient. When the diluent is a solid it may be present in lesser, equal or greater amounts than the solid active ingredient.

Usually a compound of formula (I) or (II) is administered to a subject in a composition comprising a nontoxic amount sufficient to produce an inhibition of the symptoms of a disease in which leukotrienes are a factor. Topical formulations will contain between about 0.01 to 5.0% by weight of the active ingredient and will be applied as required as a preventative or curative agent to the affected area. When employed as an oral or other ingested or injected regimen, the dosage of the composition is selected from the range of from 50 mg to 1000 mg of active ingredient for each administration. For convenience, equal doses will be administered 1 to 5 times daily with the daily dosage regimen being selected from about 50 mg to about 5000 mg.

No unacceptable toxicological effects are expected when these compounds are administered in accordance with the present invention.

The following examples are given to further illustrate the described invention. These examples are intented solely for illustrating the invention and should not be read to limit the invention in any manner. Reference is made to the claims for what is reserved to the inventors hereunder.

EXAMPLES

Characterization of Novel Human Metabolites of Pranlukast Methods

Preparation, Isolation and Characterisation of Human Metabolites

Preparation of Formula (I) Using Human Hepatic Microsomes:

The incubations were performed with a final volume of 100 mL in a shaking water bath at a temperature of approximately 37° C. Each incubation contained approximately 400 ug/mL of microsomal protein (H51), 0.5 mL 2 mM pranlukast in a 16% w/v encapsin solution containing 1.5% w/v sodium bicarbonate. The incubation volume was adjusted to 75 mL with 50 mM potassium phosphate buffer (pH 7.4). Following a 5 minute pre-incubation at approximately 37° C., the reaction was initiated by the addition of 25 mL of pre-warmed cofactor solution (approximately 1.7 mg NADP, 7.8 mg glucose 6-phosphate and 6 units of glucose 6-phosphate dehydrogenase per mL of 2% (w/v) sodium hydrogen carbonate). The reaction was terminated after 30 minutes by adding 100 mL of acetonitrile and vortex mixed. The precipitate was pelleted by centrifugation. The putative benzyl hydroxy metabolite was subsequently isolated and analysed as described below.

Preparation of the Formula (II) Using Human Hepatic Microsomes:

The incubation was performed with a final volume of 200 mL in a shaking water bath at a temperature of approximately 37° C. Each incubation contained approximately 400 ug/mL of microsomal protein (H51), 0.5 mL 2mM the 4-hydroxyphenyl analog of pranlukast in a 16% w/v encapsin solution containing 1.5% w/v sodium bicarbonate. The incubation volume was adjusted to 150 mL with 50 mM potassium phosphate buffer (pH 7.4). Following a 5 minute pre-incubation at approximately 37° C., the reaction was initiated by the addition of 50 mL of pre-warmed cofactor solution (approximately 1.7 mg NADP, 7.8 mg glucose 6-phosphate and 6 units of glucose 6-phosphate dehydrogenase per mL of 2% (w/v) sodium hydrogen carbonate). The reaction was terminated after 30 minutes by adding 200 mL of acetonitrile and vortex mixed. The precipitate was pelleted by centrifugation. The putative dihydroxymetabolite formed was subsequently analysed and isolated as described below.

Isolation and Purification of the Formula (I) and Formula (II):

The in vitro samples (approximately 200 mL for Formula (I) and approximately 400 mL for Formula (II) were freeze-dried overnight. To the dried solid, 15 mL of methanol was added and the solution was sonicated for approximately two minutes and then centrifuged (approx. 8,000×g, 10 min) on a IEC Model K Centrifuge (International Equipment Co., Needham Heights, Mass.). The supernatant was removed and the extraction repeated twice more. The supernatants were subsequently combined and the solvent was evaporated under a nitrogen stream at room temperature. The residue was reconstituted in 1.5 mL of acetonitrile:water (2:1). The solution was aliquoted into 15 vials of approx. 100 uL solution each and was analyzed using the HPLC system and conditions described above. The eluent from repeat injections was collected (from the UV detector outlet) into vials at 0.4 min intervals using a Foxy fraction collector (ISCO, Lincoln, Nebr.). The desired fractions for collection were determined based on the UV chromatogram. The combined fractions were freeze-dried and the residue was loaded onto a C18-Mega Bond Elut (Analytichem International, Harbor City, Calif.). The column was washed with water (approximately 4 mL) to remove residual salt from the sample. The metabolite was then eluted from the column with methanol (approximately 4 mL). Solvent was removed from the sample under a stream of nitrogen and then lyophilized prior to storage for NMR analysis. The purified sample was stored in a dessicator prior to NMR analysis. This purification procedure was verified by using [$^{14}$C]SB 205312 in a small scale incubation to ensure that all the extraction steps were quantitative.

Qualitative HPLC-MS and HPLC-MS-MS Analysis
Sample Preparation:

Samples from the human S9 incubations were received as a 1:1 mixture of incubation media and acetonitrile. In order to reduce the relative organic content to about 25%, the samples were diluted with an equal volume of water prior to HPLC/MS and HPLC/MS/MS analysis. Samples from the microsomal incubations were also received as a 1:1 mixture of incubation media and acetonitrile. The relative organic content was however reduced to about 25% by evaporation following the centrifugation step.

HPLC conditions for LC/MS analyses:
HPLC pumps: Hitachi L6200A and L6000
HPLC autosampler ThermoSeparations AS3000
Column Waters Symmetry C8 (150×3.9 mm), 5 um particle size
Guard Column Waters Symmetry C8 (30×2.0 mm), 5 um particle size
Solvent A: 10 mM ammonium formate pH 4.0
Solvent B: acetonitrile
HPLC flow rate: 1.0 mL.min$^{-1}$
Temperature: ambient
Split ratio into the MS: approximately 9.5:1
Gradient conditions:

| Time (min) | % A | % B |
| --- | --- | --- |
| 0 | 95 | 5 |
| 60 | 30 | 70 |
| 61 | 0 | 100 |
| 62 | 0 | 100 |
| 65 | 95 | 5 |
| 85 | 95 | 5 |

Mass Spectrometry:
Mass Spectrometer: Finnigan TSQ700 Triple Quadrupole Mass Spectrometer
Data System: Personal DECStation running ICL (v.7.4) and ICIS(v.7.0) Ionization
Mode: Electrospray (operating in the negative ionization mode)
Scanning: 200–800 amu, 2 sec/scan (single quad scans)
Collision Gas: Argon, 2 mTorr
Collision Energy: 25 eV As indicated above, the column effluent was split such that a flow of 50 uL/min was directed into the mass spectrometer. The remainder was directed into the 125 uL solid flow cell of a Beckman 171 Radioisotope Detector.

Multiple reaction monitoring was conducted for the human microsomal samples. The following transitions, 496→292, for Formula (I), and 512→294, for Formula (II), were monitored by alternately allowing n/z 496 and m/z 512 to pass through Q1 into the collision cell while simultaneously setting Q3 to allow only the appropriate fragment mass (292 or 294) to pass through to the detector.

Nuclear Magnetic Resonance (NMR) Spectroscopy

The proton NMR spectra of the pranlukast metabolites were measured at 400.13 MHz, using a Bruker Instruments AMX400 spectrometer which was equipped with an inverse gradient multinuclear probe maintained at 25° C. Samples ranging from 150 ug to 200 ug were dissolved in 0.5 mL of deuterated pyridine (Aldrich Chemical Co., Milwaukee, Wis.) using tetramethylsilane as an internal reference. A spectral width of 5435 Hz was measured using 32K data points. Each spectrum resulted from signal averaging 48 scans. Proton nuclear Overhauser experiments (nOe) were measured by selectively irradiating the methine at 5.13 ppm and the methylene at 4.01ppm, along with an off-resonance control frequency, with low RF power for seven seconds prior to acquisition. For each spectrum, 256 scans were signal averaged at the selected frequency, then the process repeated 8 times leading to 2048 scans per irradiation. Following Fourier transformation, difference spectra were generated by subtracting the off-resonance control spectrum from each irradiated spectrum.

In order to confirm proton connectivity, a COSY 2-dimensional experiment was measured for the sample. The experiment from the AMX microprogram library employed the "cosy" pulse program. The 512 spectra in the F2 dimension were measured using 1024 data points over a spectral width of 6024 Hz. The incrementable delay was increased in successive spectra to achieve a spectral width of 6024 Hz in the F1 dimension. For each spectrum, 64 scans were signal averaged with a pulse delay of 1 s between successive spectra.

RESULTS

Identification of Pranlukast Human Hepatic Metabolites

The negative electrospray ionization mass spectra of pranlukast and associated compounds are characterized by a deprotonated molecule of the type [M-H]$^-$. Collision induced dissociation of these compounds was generally characterized by three predominant processes: loss of the tetrazole nitrogens as molecular $N_2$, loss of the butyl phenyl group, and amide bond cleavage. The means by which the butyl phenyl group was lost appeared to be sensitive to the degree, and possibly the position, of hydroxylation. For example, following the loss of the tetrazole group by expulsion of molecular nitrogen, pranlukast appeared to lose the butyl phenyl group via homolytic bond cleavage (m/z 291). A homolytic process also appeared to be responsible for the ion resulting from amide bond cleavage (m/z 171) for pranlukast. Incorporation of a single hydroxyl group in either the 3- or 4-positions of the phenyl ring yielded a structure which favored heterolytic bond cleavage resulting in even electron ions. Thus, the loss of the butyl phenyl group and amide bond cleavage produced ions at m/z 292 and 172, respectively. Incorporation of a hydroxyl groups at both the 3- and 4-positions of the pheny ring also yielded a structure in which the dominant fragmentation modes appeared to involve heterolytic bond cleavage. However, loss of the butyl phenyl group in the case of the 3,4-dihydroxyphenyl analog of pranlukast used as the standard, resulted in a ion at m/z 294. This fragmentation may be rationalized by the presence of the ortho-hydroxyl groups which could each transfer a hydrogen atom to the carbene (resulting from loss of the trazole nitrogens). Elimination of the resulting alkyl quinone would yield an ion at m/z 294.

Incubation of pranlukast with human liver S9 from donor H51 demonstrated the formation of two major metabolites of pranlukast, nominated MM4 and MM5, which were both dependent on the presence of NADPH. Retention times observed in the ion chromatograms for m/z 498 and 482 (pranlukast) correlate well with those in the radiochromatogram. MM4 and MM5 showed parent ions at m/z 498 indicating that both metabolites were products of monooxygenation. Note that the specific activity of the incubation sample was such that the predominant ionic species were observed at 2 amu higher than the nominal $^{12}$C-monoisotopic mass. Therefore, in the CID spectra of the two monohydroxylated metabolites and the parent compound, the precursor and fragment ions are all shifted by +2 amu due to the predominance of the [$^{14}$C] label. The observed fragmentation patterns are identical to the standards and confirmed the presence of pranlukast, as well as two monohydroxylated metabolites.

The early eluting peak, MM4, demonstrated fragments of m/z 294 and 174, consistent with oxygen incorporation in the alkyl phenyl region of the parent molecule. The formation of a 3-hydroxyphenyl or 4-hydroxyphenylcompound could be ruled out on the basis of retention time. The proton NMR spectrum of isolated MM4 was compared to the proton NMR spectrum of pranlukast. The aromatic regions were identical except for slight differences in the chemical shifts of the proton signals of the mono-substituted phenyl group. In the reference spectrum, the mono-substituted phenyl ring spin-system (H2"–H4") is contained in the region from $\delta$7.22 to $\delta$7.38. The metabolite spectrum indicates that the multiplets for H4" and H2" range from $\delta$7.30 to $\delta$7.45, while H2" is shifted to $\delta$7.69 relative to the reference spectrum consistent with a change at position 8'. The aliphatic region of the reference spectrum of pranlukast displays H5' and H8' as triplets at $\delta$3.9 1 and $\delta$2.64, respectively. For the metabolite spectrum, the aliphatic region of the spectrum displays H8' as a one-proton doublet of doublets at $\delta$5.12, which represents a dramatic down-field shift of ca. $\delta$2.5. The chemical shift of the oxymethylene, H5', is shifted about $\delta$0.2. The data at this point indicate that hydroxylation occurred at position 8' in the metabolite. Further confirmation was obtained through decoupling and nOe difference experiments. In the decoupling experiments, both H8' and H5' were irradiated. Irradiation of H8', resulted in sharpening the doublet of multiplets at $\delta$7.69, H2", indicating allylic coupling and providing additional evidence that hydroxylation occurred at H8'. Irradiation of H5' did not result in changes in the aromatic region of the spectrum. Irradiation at both positions, H8' and H5', resulted in changes in the region of overlapping multiplets, $\delta$2.2–$\delta$2.0. For the nOe experiments, saturation of H5' enhanced H3' of the oxybenzamide group, while saturation of H8', resulted in the enhancement of H2" of the mono-substituted phenyl group, confirming that the hydroxyl group is located at position 8' [Formula (I)].

A novel dihydroxy metabolite was found in human fecal samples which did not co-chromatograph with the 3,4-dihydroxyphenyl standard. Therefore, incubation of the 4-hydroxyphenyl pranlukast analog with human liver microsomes and NADPH was conducted in order to confirm the identity of this metabolite. As illustrated by the reconstructed ion chromatograms of m/z 496 (the 4-hydroxyphenyl analog) and m/z 512 (dihydroxylated metabolite), LC/MS analysis suggested that a metabolite with chromatographic retention time identitical to the novel fecal metabolite had been generated in vitro. Background subtracted mass spectra derived from the peaks in the ion chromatograms, were consistent with the presence of the 4-hydroxyphenyl analog and a dihydroxylated metabolite. Further structural characterization of the metabolite was provided by MS/MS. The presence of m/z 292, as opposed to m/z 294, in the CID spectrum of m/z 512 suggested a structure hydroxylated on the alkyl chain as well as on the aromatic ring. Based on the metabolism of pranlukast (vide supra), a likely site of hydroxylation of the 4-hydroxyphenyl analog would be at the benzylic position. The proton NMR spectrum of MM9 was compared to the proton NMR reference spectrum of the 4-hydroxyphenyl compound. The aromatic regions were identical except for the proton signals of the 4-hydroxy-phenyl group. In the reference spectrum, the 4-hydroxy-phenyl ring, an $A_2B_2$ spin-system including H2" and H3" protons, is contained in the region from $\delta$7.25 to $\delta$7.19. The analogous metabolite spectrum indicates a larger separation between protons H2" and H3", which are located at $\delta$7.60 and $\delta$7.31, respectively. The relatively large shift for proton H2" (ca. $\delta$0.36) relative to the same signal in the reference spectrum is consistent with a change at position 8'. The aliphatic region of the reference spectrum of the 4-hydroxyphenyl compound displays H5' and H8' as triplets at $\delta$3.91 and $\delta$2.64, respectively. For the MM9 spectrum, however, the aliphatic region of the spectrum displays H8' as a one-proton doublet of doublets at $\delta$5.12, which represents a dramatic down-field shift of ca. $\delta$2.5. The chemical shift of the oxymethylene, H5', is shifted about $\delta$0.2. The chemical shift for H8' is consistent with the proton of a benzylic methine bearing a hydroxyl group. Further confirmation of the position of hydroxylation was obtained through decoupling and nOe difference experiments. In the decoupling experiments, both H8' and H5' were irradiated. Irradiation of H8', resulted in sharpening the doublet at $\delta$7.60, H2", indicating allylic coupling and providing evidence that supports hydroxylation at H8'. Irradiation of H5' did not result in changes in the aromatic region of the spectrum. Decoupling at both positions, H8' and H5', resulted in changes in the region of overlapping multiplets, $\delta$2.2–$\delta$2.0, which contains methylene protons H6' and H7'. For the nOe experiments, saturation of H5' enhanced H3' of the oxybenzamide phenyl ring, while saturation of H8', resulted in the enhancement of H2" of the 4-hydroxy phenyl group, confirming that the hydroxyl group is located at position 8'.

SYNTHETIC EXAMPLES

Example 1

Preparation of 4-Oxo-8-[4-(4-Hydroxy-4-Phenylbutoxy)Benzoylamino]-2-Tetrazol-5-yl-4H-1-Benzopyran 2-Phenyl-2-(3-Chloropropyl)-1,3-Dioxolane 4-Chlorobutyrophenone (15.18 g, 0.083 moles), ethanediol (6.80 g, 0.110 moles) and p-toluene sulphonic acid (0.20 g) were heated in toluene at reflux and water was removed from the reaction using a Dean and Stark apparatus. After 17 hours the solvent was removed by distillation in vacuo to leave crude 2-phenyl-2-(3-chloropropyl)-1,3-dioxolane (21 g).

NMR (CDCl$_3$) ppm, 1.85, 2H, m; 2.03, 2H, m; 3.50, 2H, t; 3.74, 2H, m; 3.98, 2H, m; 7.31, 3H, m; 7.42, 2H, dd.

Methyl 4-(4-oxo-4-Phenylbutoxy)Benzoate Ethylene Acetal.

Crude 2-phenyl-2-(3-chloropropyl)-1,3-dioxolane (21.0 g), potassium carbonate (14.0 g; 0.101 moles) and methyl 4-hydroxybenzoate (14.0 g, 0.092 moles) were heated in dimethylformamide (100 ml) for 21 hours. The mixture was diluted with water (250 ml) and extracted with dichloromethane (500 ml). The dichloromethane extract was washed with saturated sodium bicarbonate solution and then with water. The organic extract was concentrated in vacuo to give the product as a brown solid (27.3 g).

MS (e.i.) m/z (%) 77 (43), 105 (93), 149 (100), 265 (40), 342 (10).

NMR (CDCl$_3$) ppm, 1.89, 2H, m; 2.07, 2H, m; 3.79, 2H, t; 3.98, 3H, s; 4.00, 4H, m; 6.86, 2H, d; 7.29–7.51, 5H, m; 7.95, 2H, d.

4-(4-Oxo-4-Phenylbutoxy)Benzoic Acid Ethylene Acetal.

Methyl 4-(4-oxo-4-phenylbutoxy)benzoate ethylene acetal (27.0 g), denatured alcohol (90 mls), water (90 ml) and sodium hydroxide (9.0 g, 0.225 moles) were heated at reflux for 3 hours. The mixture was cooled to 20° C., diluted with water (250 ml) and extracted with toluene (2×250 ml). The aqueous phase was acidified with concentrated hydrochloric acid (35 ml) and the precipitate filtered, washed with water and dried to give 4-(4-oxo-4-phenylbutoxy)benzoic acid ethylene acetal (21.1 g, 70% from 4-chlorobutyrophenone).

MS (Negative ion ionspray) m/z [M-H]$^-$ 327

NMR (DMSO-d$_6$) ppm, 1.72, 2H, m; 1.98, 2H, m; 3.70, 2H, t; 4.00, 4H, m; 6.94, 2H, d; 7.23–7.96, 5H, m; 7.84, 2H, d; 12.5, 1H, br.s.

4-Oxo-8-[4-(4-Oxo-4-Phenylbutoxy)Benzoylaminol-2-Tetrazol-5-yl-4H-1-Benzopyran Ethylene Acetal.

4-(4-Oxo-4-phenylbutoxy)benzoic acid ethylene acetal (7.5 g, 0.023 mole), thionyl chloride (3.26 g, 0.027 mole) and dimethylformamide (20 mg) were heated in dichloromethane (75 mls) at reflux for 2 hours. The solvent was removed in vacuo and the residue, pyridine (5.38 g, 0.068 mole) and 8-amino-4-oxo-2-tetrazol-5-yl-4H-1-benzopyran (SB-241906: 5.34 g, 0.023 mole) were heated in toluene (50 mls) at 100° C. for 90 minutes. The reaction was cooled to 20° C. and dilute hydrochloric acid added. The crude product was filtered and the wet cake dissolved in warm methanol (100 ml) and sodium acetate (2.0 g, 0.024 mole). Insoluble matter was removed by filtration and the supernatant liquor acidified with concentrated hydrochloric acid (2.5 mls). The precipitate was filtered, washed with methanol and dried to give the title compound (12.7 g 103%).

MS (Positive ion ionspray) m/z (%) 105 (18), 121 (12), 147 (100), 175 (21), 191 (29), 496 (41), 512 (15), 540 (96).

NMR (DMSO-d$_6$) ppm, 1.77, 2H, m; 2.02, 2H, m; 3.70, 2H, t; 7.07, 2H, d; 7.13, 1H, s; 7.30–7.47, 5H, m; 7.56, 1H, t; 7.91, 1H, d; 8.03, 2H, d; 8.29, 1H, d; 7.96, 1H, s.

4-Oxo-8-[4-(4-Oxo-4-Phenylbutoxy)Benzoylamino]-2-Tetrazol-5-yl-4H-1-Benzopyran

4-Oxo-8-[4-(4-oxo-4-phenylbutoxy)benzoylamino]-2-tetrazol-5-yl-4H-1-benzopyran_ethylene acetal (12.5 g, 0.023 moles) water (20 ml) and p-toluene sulphonic acid (200 mgs) were heated in acetone (700 ml) at reflux for 16 hours. The reaction was cooled to 20° C. and filtered to give 4-oxo-8-[4-(4-oxo-4-phenylbutoxy)benzoylamino]-2-tetrazol-5-yl-4H-1-benzopyran (5.04 g, 44%).

MS (Positive ion ionspray) m/z (%) 105 (22), 147 (100), 175 (12), 266 (6), 294 (18), 350 (5), 468 (6), 496 (46).

NMR (DMSO-d$_6$) ppm, 2.13, 2H, m; 3.23, 2H, t; 4.18, 2H, t; 7.13, 3H, m; 7.50–7.69,4H, m; 7.91,2H, d; 8.02, 4H, m; 8.29, 2H, d; 9.98, 1H, s.

4-Oxo-8-4-(4-Hydroxy-4-Phenylbutoxy)benzoylamino]-2-Tetrazol-5-yl-4H-1-Benzopyran Sodium borohydride (1.45 g) was added, in portions to 4-oxo-8-[4-(4-oxo-4-phenylbutoxy)benzoylamino]-2-tetrazol-5-yl-4H-1-benzopyran (5.0 g, 0.010 mole) in methanol (100 ml) at 20° C. The reaction was diluted with water (400 ml) and 1 M hydrochloric acid (35 ml) added. The solid was filtered, washed with water and dried at 80° C. to give 4-oxo-8-4-(4-hydroxy-4-phenylbutoxy)benzoylamino]-2-tetrazol-5-yl-4-benzopyran (4.95 g, 98%).

Mpt. 198–205° C.

IR (Nujol mull) cm$^{-1}$, 3300 (m), 1659 (s), 1642 (s), 1605 (m), 1584 (m), 1527 (m), 1506 (s), 1463 (s), 1430 (s), 1377 (s), 1289 (s), 1252 (s), 1179 (m), 1036 (m), 765 (m).

MS (Positive ion ionspray) m/z (%) 131 (100), 147 (26), 175 (28), 228 (7), 251 (31), 396 (6), 424 (100), 435 (19), 452 (15), 480 (50), 498 (28).

NMR (Pyridine-d$_5$) ppm 2.00–2.20, 4H, m; 4.03, 2H, m; 5.09, 1H, m; 7.06, 2H, d; 7.29–7.47, 4H, m; 7.70, 2H, m; 8.17, 1H, d; 8.51, 2H, d; 8.94, 1H, d; 10.25, 1H, s.

What is claimed is:

1. A compound of formula I in essentially pure form

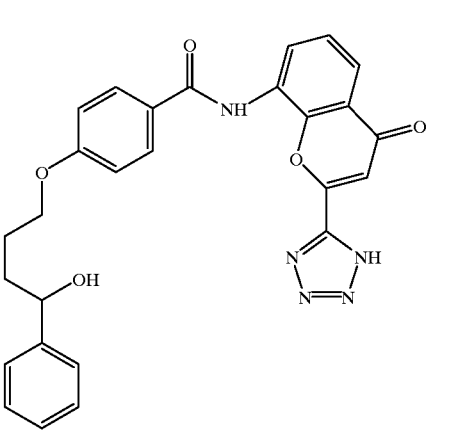

(I)

or a pharmaceutically acceptable salt thereof; or an enantiomer thereof, a hydrate, solvate or a polymorph thereof.

2. A compound of Formula II in essentially pure form

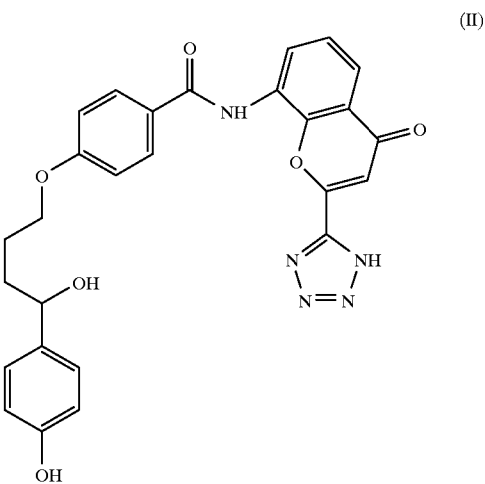

(II)

or a pharmaceutically acceptable salt thereof; or an enantiomer, a solvate, a hydrate or a polymorph thereof.

3. A pharmaceutical composition comprising a compound of Formula I in essentially pure form

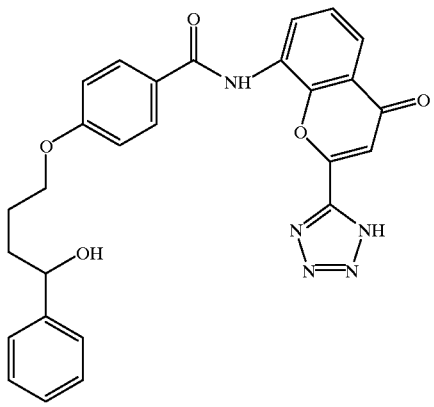

or a pharmaceutically acceptable salt thereof; or an enantiomer, a solvate, a hydrate or a polymorph thereof; and a pharmaceutically acceptable excipient.

4. A pharmaceutical composition comprising a compound of Formula II in essentially pure form

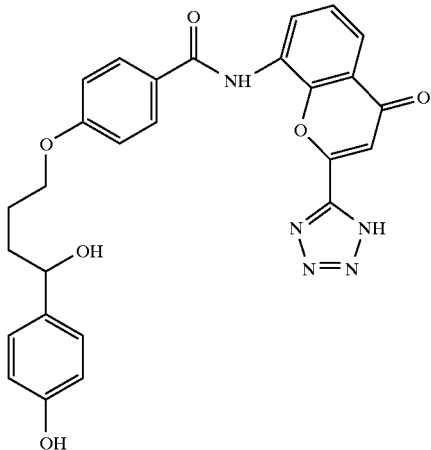

or a pharmaceutically acceptable salt thereof; or an enantiomer, a solvate, a hydrate or a polymorph thereof; and a pharmaceutically acceptable excipient.

5. A method for treating asthma comprising administering to a mammal in need thereof a pharmaceutically acceptable composition comprising a pharmaceutically acceptable excipient and an essentially pure form of formula (I) or (II).

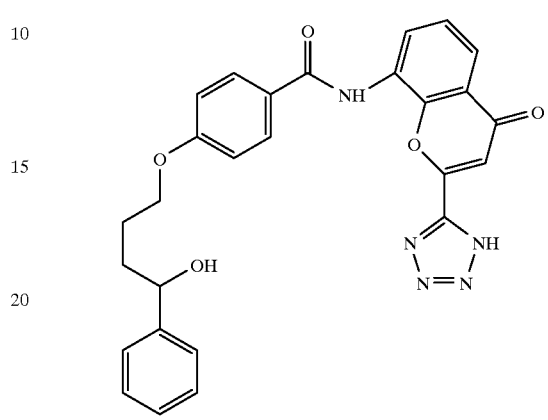

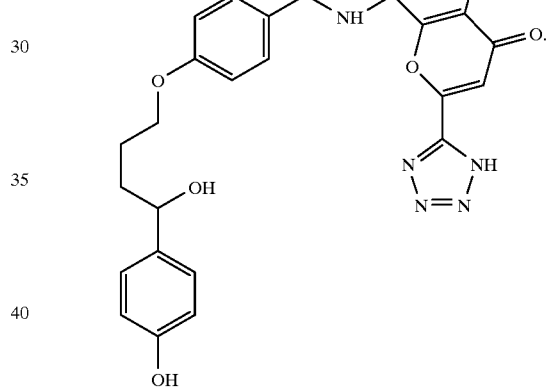

6. A method for manufacturing a pharmaceutical composition comprising mixing a compound according to claims 1 or 2 with a pharmaceutically acceptable excipient.

* * * * *